Figure 1:
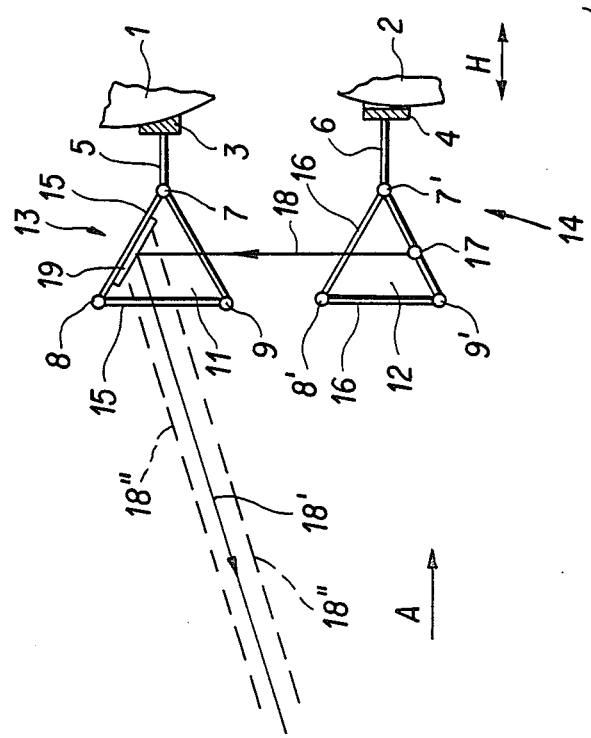

United States Patent [19]

Neumeyer

[11] Patent Number: 4,859,181

[45] Date of Patent: Aug. 22, 1989

[54] METHOD AND APPARATUS FOR MEASURING RELATIVE JAW MOVEMENT

[76] Inventor: Stefan Neumeyer, Leminger Str. 10, 8491 Eschlkam, Fed. Rep. of Germany

[21] Appl. No.: 95,082

[22] Filed: Sep. 11, 1987

[30] Foreign Application Priority Data

Sep. 11, 1986 [DE] Fed. Rep. of Germany ....... 3630945
Oct. 28, 1986 [DE] Fed. Rep. of Germany ....... 3636671

[51] Int. Cl.⁴ .............................................. A61C 19/04
[52] U.S. Cl. ....................................... 433/69; 128/777
[58] Field of Search ................... 433/69, 68; 128/777; 356/373, 375

[56] References Cited

U.S. PATENT DOCUMENTS 4,330,276  5/1982  Becker et al. ........................ 433/69
4,447,207  5/1984  Kataoka et al. ...................... 433/69
4,673,352  6/1987  Hansen ................................ 433/69

OTHER PUBLICATIONS

"Interocclusal Distance Measurement Comparing Chin and Tooth Reference Points", Ekfeldt et al., Jo. of Pros. Dent., 5/1982, vol. 47, No. 5.

"Recording of Mandibular Movements by Intraorally Placed LEDs", Karlsson, vol. 35, Acta. Odont. Scan., 111 (1977).

"Real Time Monitoring of the Movement of the Mandible", Curry et al., Proceedings 4-American Society of Photogrammetry, 99, 1986.

Primary Examiner—John J. Wilson
Attorney, Agent, or Firm—Hoffman, Wasson, Fallow & Gitler

[57] ABSTRACT

A process and apparatus for three-dimensional determination of the relative movement between the upper and lower human jaws by affixing at least one reference element to each of the jaws, one of the reference elements having four spatially staggered reference marks and the other having at least three spatially staggered reference marks. The position of each reference marks is optically detected along at least two viewing axes. The relative movement of the jaws is then determined from the change in the mutual position of the reference marks.

12 Claims, 7 Drawing Sheets

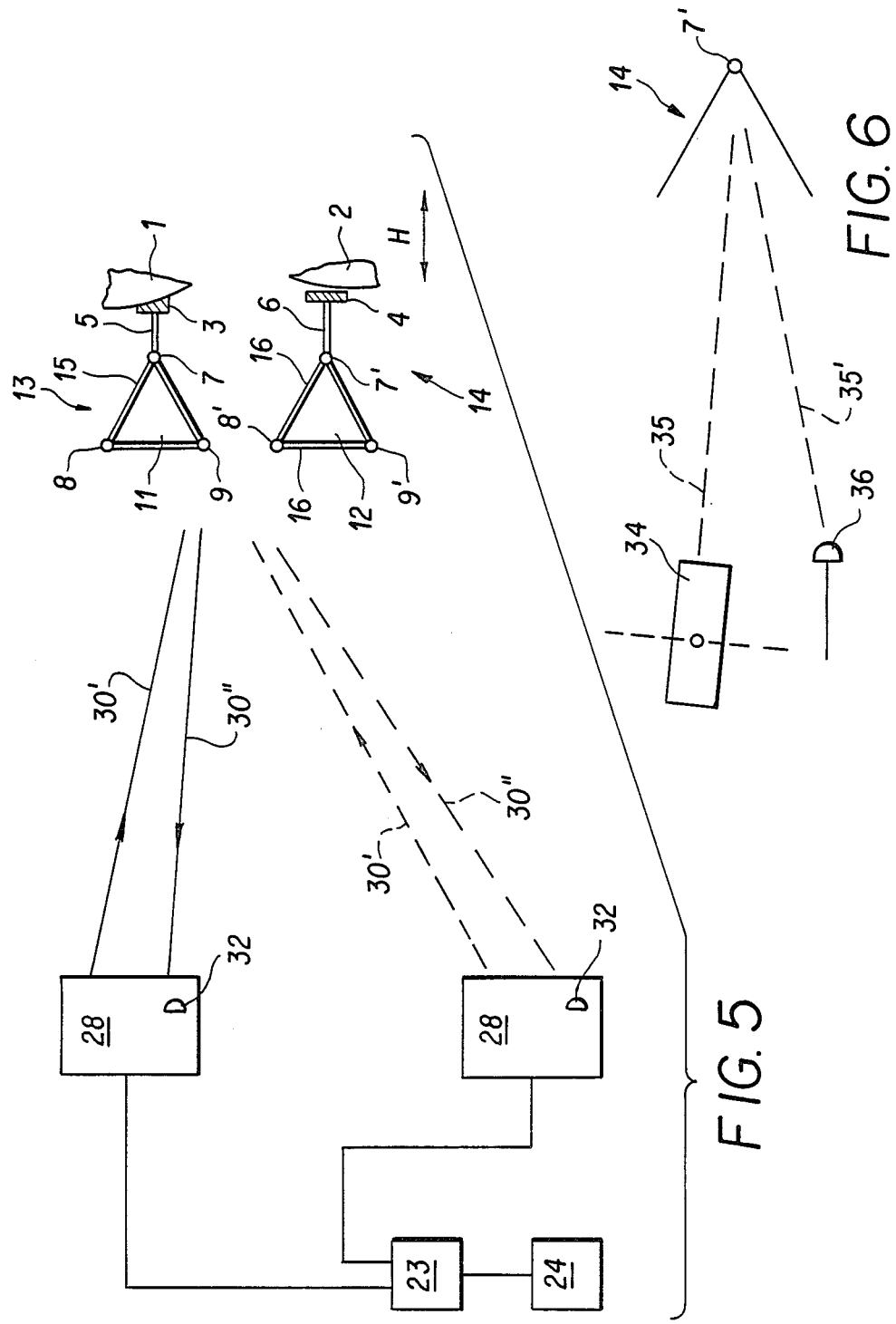

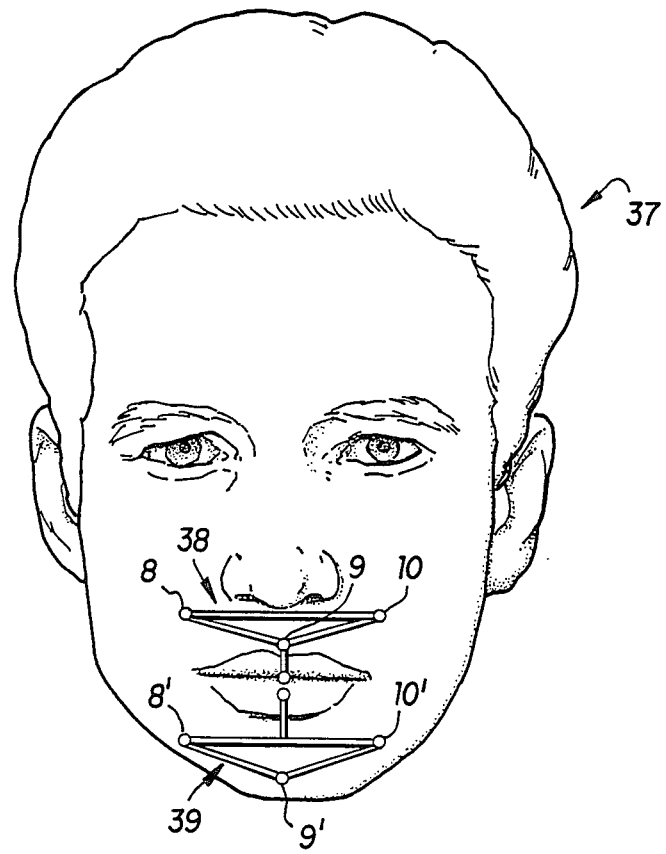
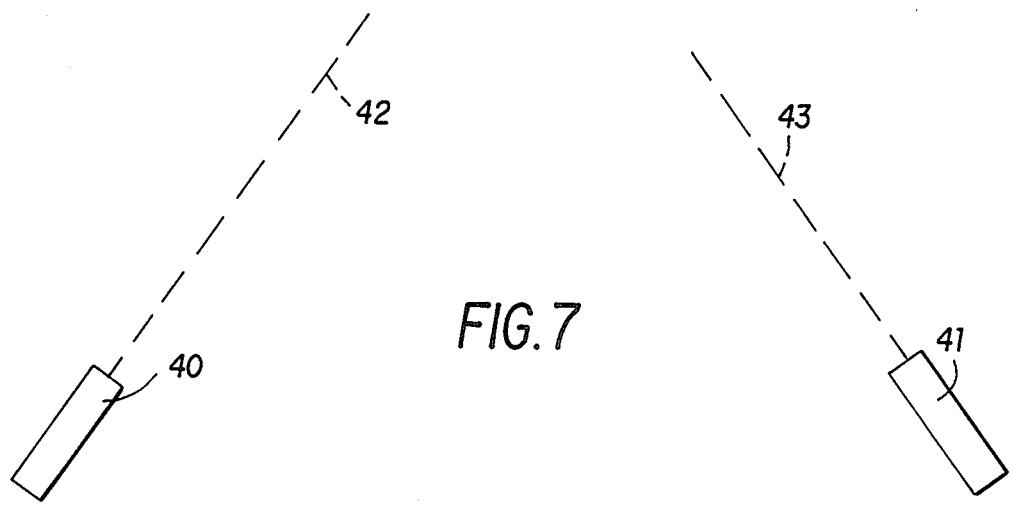
FIG. 7

METHOD AND APPARATUS FOR MEASURING RELATIVE JAW MOVEMENT

The invention relates to a process for at least two-dimensional determination of the relative movement between an upper jaw and a lower jaw and to a measuring arrangement for embodying this process.

In dental technology and dental medicine it is often necessary to measure the movement of the lower jaw relative to the upper jaw and to store the data obtained. This is especially necessary when the jaw movement is to be simulated in a so-called "articulator," for which to start with it is necessary to determine the respective position and movement of the lower jaw relative to the upper jaw of a patient and to transfer the values thus determined to the articulator or to compare them with the simulated movements in this articulator.

For the determination of the relative movement between the human lower jaw and the human upper jaw, devices have already been suggested which are designed in principle so that on both sides of a patient's skull, in the region of the jaw joints, measuring arrangements are placed which each consist of two transmitter elements, one of which is connected with the upper jaw and one with the lower jaw, and in each measuring arrangement the relative movement between the two transmitter elements is determined in three axial directions. These known devices or measuring arrangements have the disadvantage, among others, that due to the system the measuring results obtained with these arrangements are not error-free, the placement of the transmitter elements, especially on the lower jaw of a patient, is not without problems and, above all, due to cumbersome equipment the natural movement of the lower jaw relative to the upper jaw is practically, at least psychologically, hindered.

The object of the invention is thus to demonstrate a process for at least two-dimensional determination of the relative movement between an upper jaw and a lower jaw and a measuring arrangement for embodying this process which, with simple means, leads to substantially more precise results and above all makes possible the direct determination of the relative movement between the lower jaw and the upper jaw.

To solve this task, a process according to the invention corresponding to the characterizing section of claim 1 and a measuring arrangement for embodying this process corresponding to the characterizing section of patent claim 15 is designed.

In the process according to the invention, the at least two-dimensional determination of the relative movement between the upper jaw and the lower jaw occurs preferably in that, on the side of this jaw facing the optoelectric device in a two-dimensional determination of the movement at least two, and in a three-dimensional determination of the movement at least three or four spatially staggered reference marks are placed on each jaw and in the latter case the mutual position the reference marks exhibit on each jaw and the position of the reference marks on one jaw relative to the reference marks on the other jaw, as well as the changes in these positions, are optically detected and from this, preferably by using a computer (computer-aided), the relative movement of both jaws is determined.

In one embodiment of the invention the optical detection of the mutual position of the reference marks and the change in this position occurs with the aid of at least one video camera, preferably with at least one color video camera and in the electrical frames provided by this camera, preferably after intermediate storage in an image storage device, the available reference marks and their mutual positions are determined and the data which describe the position of the reference marks for the determination of the relative movement between the jaws are evaluated in a computer according to a preset program.

The localization of the reference marks in the electrical frames can thus occur, for example, in that these frames are each scanned by line and column according to the reference marks which stand out prominently from the remaining video signal or frame contents. As a criterion for the localization of the reference marks in the frames, a particular brightness and/or a particular coloration of the reference marks are suitable.

In another embodiment of the invention, the optical detection of the mutual position of the reference marks and the change in this position occurs with the aid of at least one laser device which emits at least one laser beam and with this laser beam the measuring area formed by the reference marks is scanned by line and column. Only when the scanning laser beam strikes a reference mark does the reference mark reflect a part of the laser beam on a light detector provided on the optoelectric device. From the solid angle exhibited by the scanning laser beam each time it intersects a beam reflected on the light detector relative to an original position, optionally using additional remote measurement between the laser device and the respective reference mark, the position of this reference mark is determined and stored in a memory. From stored data of all reference marks, the relative position which the reference marks or both jaws exhibit toward each other and the relative movement of these jaws can be determined. Especially in the determination of the relative movement between the lower jaw and the upper jaw, at least four of the reference marks are formed on each reference element.

"At least two-dimensional determination of the relative movement" means a determination of the relative movement in at least two space axes which run perpendicular to each other. "Observation axis" means the axis in which the measuring area formed by the reference marks is detected by the optoelectric device.

Further developments of the invention are the subject of the subclaims.

Figure 2:
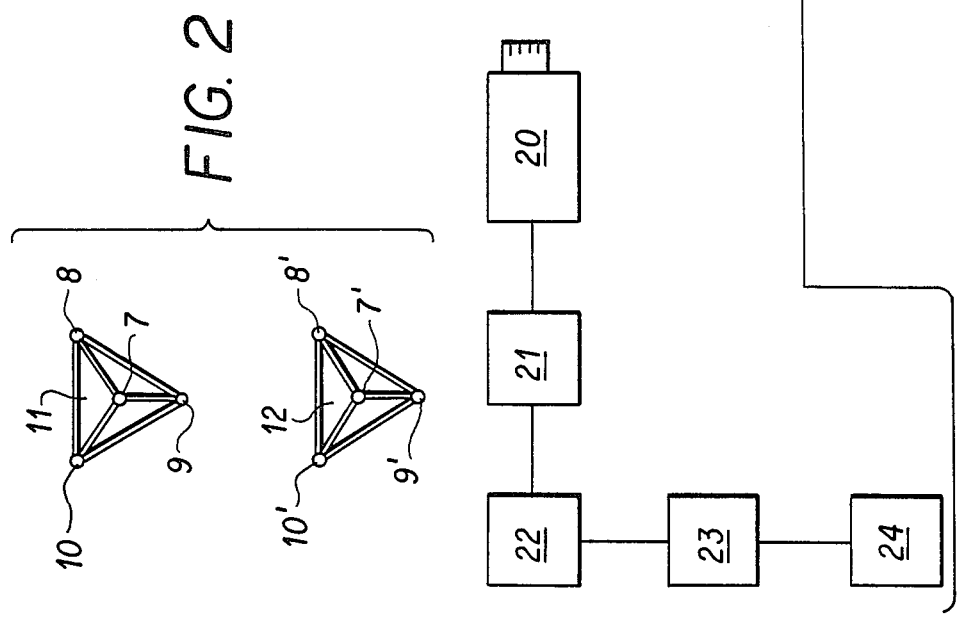
Figure 3:
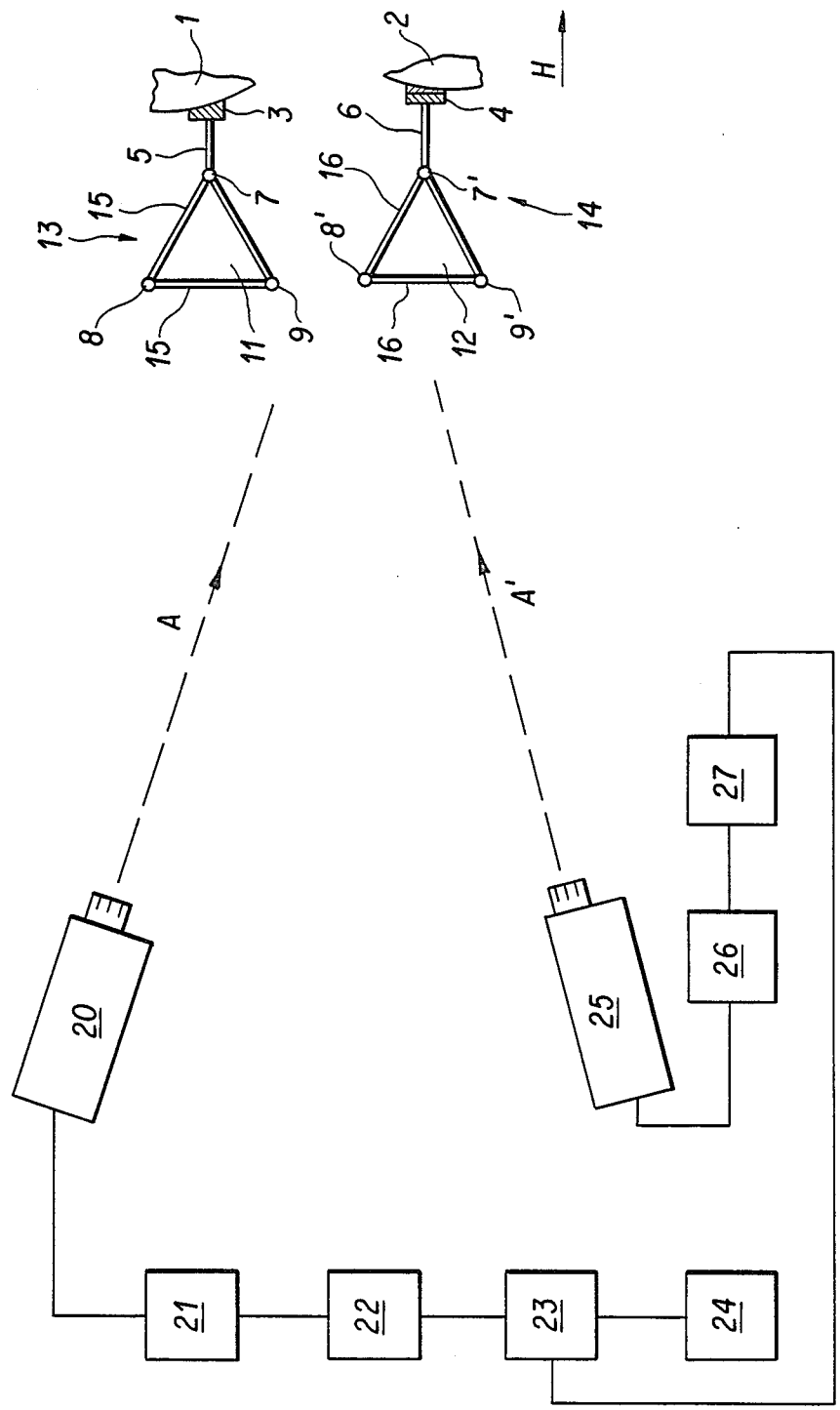
Figure 4:
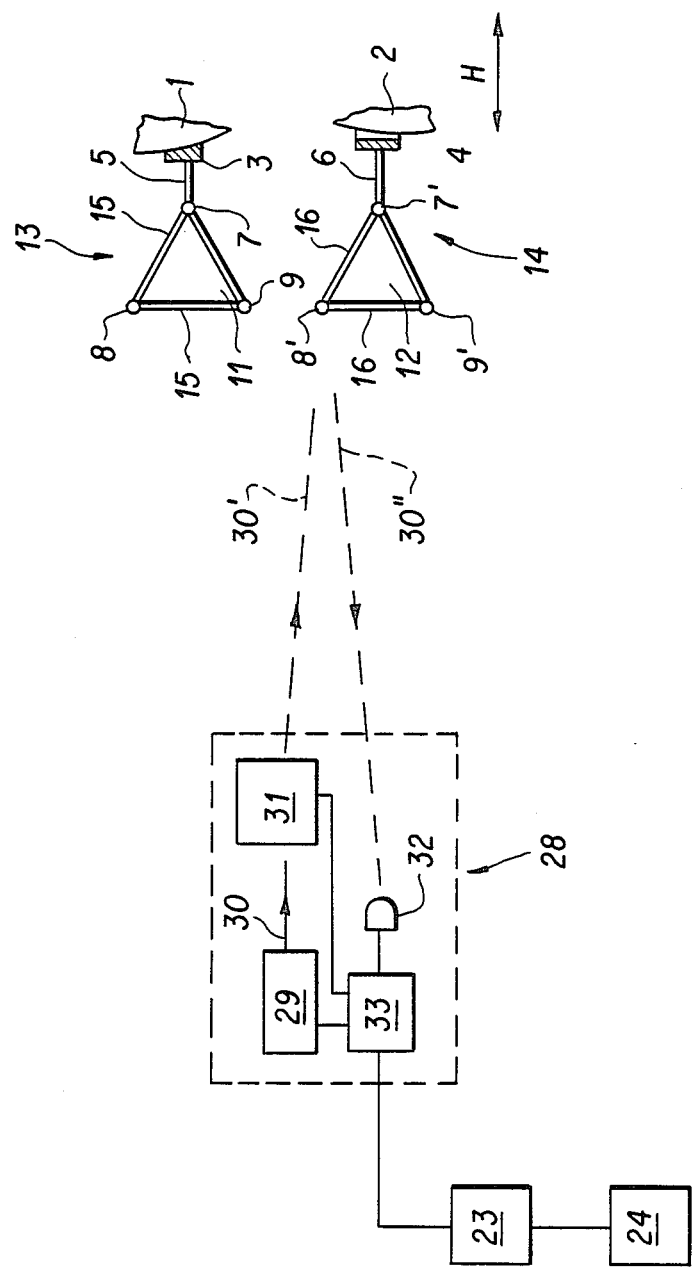
Figure 8:
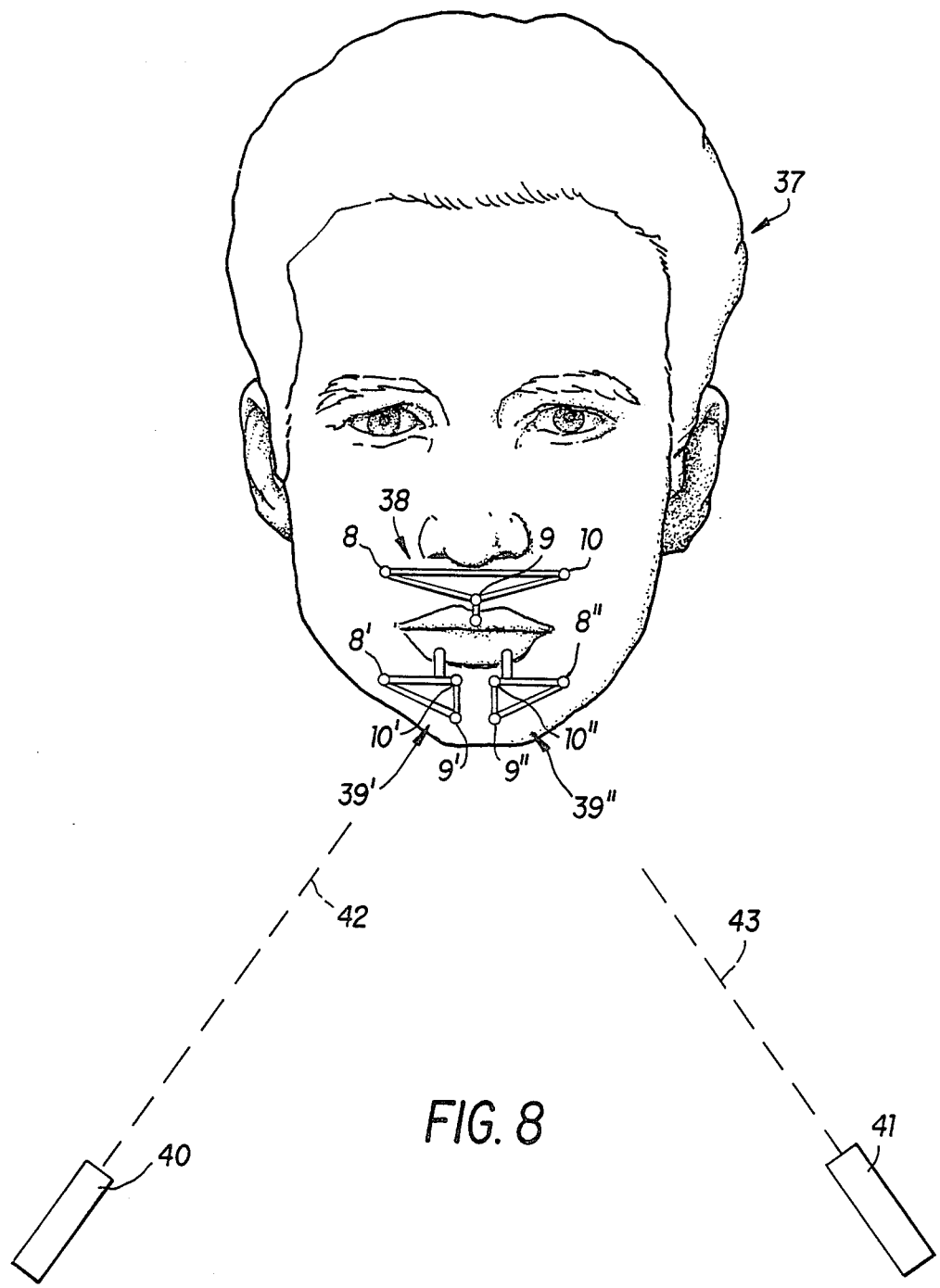
Figure 9:
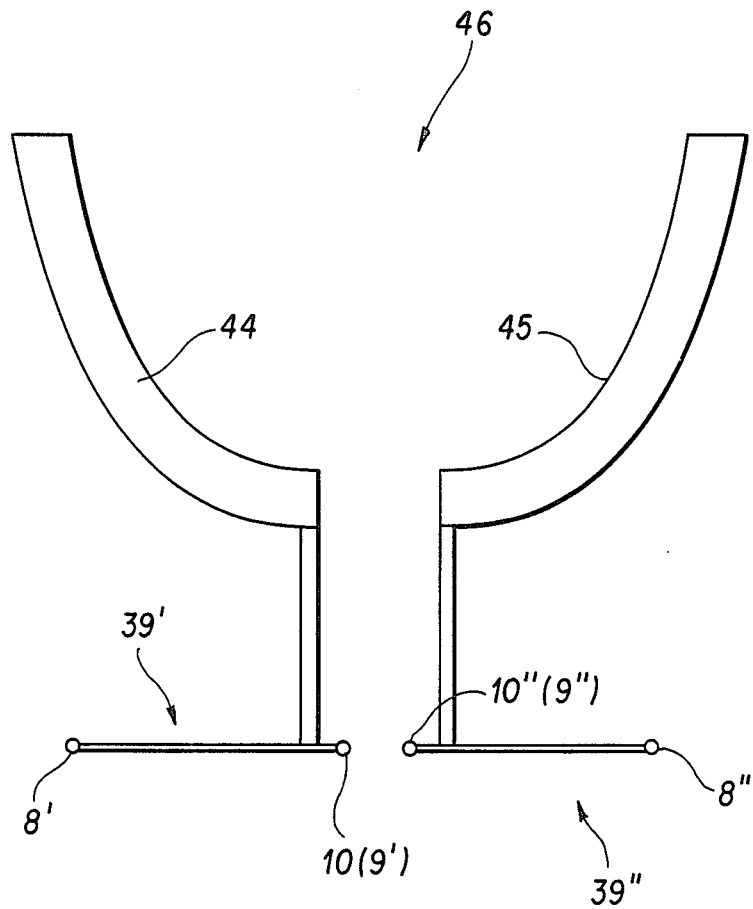

The invention will be further explained in the following based on the figures on one embodiment. Shown are:

FIG. 1 A diagrammatic drawing of the design of a measuring arrangement for three-dimensional determination of the relative movement between the human upper jaw and the lower jaw in a side view using a video camera;

FIG. 2 The reference marks of the measuring arrangement placed on the front teeth or incisors of a human upper or lower jaw according to FIG. 1 in the viewing direction of arrow A in FIG. 1;

FIG. 3 A diagrammatic drawing of a measuring arrangement using two video cameras;

FIG. 4 A diagrammatic drawing of a measuring arrangement using a laser device;

FIG. 5 A diagrammatic drawing of a measuring arrangement using two laser devices;

FIG. 6 A diagrammatic drawing of a further embodiment of the measuring arrangement with laser device;

FIGS. 7 to 9 A diagrammatic drawing of further embodiments of the measuring arrangement.

The measuring arrangement shown in FIG. 1 is for three-dimensional measurement of the relative movement between the upper jaw and the lower jaw of a patient, and because of the simpler drawing only a single incisor 1 or 2 each is shown from the upper jaw and the lower jaw. On the front side of the existing incisors 1 of the upper jaw, a striated, curved holding element 3, preferably one made of thermoplastic material, is fastened by gluing or by another suitable way. A similarly designed holding element 4 is fastened on the front side of incisors 2 on the lower jaw. On the surface side facing away from incisors 1 or 2, each holding element 3 or 4 has a rodlike element 5 or 6, which extends outward with its free end above the holding element concerned, lies longitudinally perpendicular to the surface sides of the holding element involved and is connected, on its free end, to one vertex 7 or 7' of a pyramidlike body 11 or 12 which exhibits a total of four vertices 7, 8, 9, and 10 or 7', 8', 9', and 10'. Pyramidlike body 11 with vertices 7-10 forms, together with rodlike element 5 and holding element 3, the one reference element 13 and pyramidlike body 12 with vertices 7'-10', together with rodlike element 6 and holding element 4, forms the other reference element 14 of the measuring arrangement. Both reference elements 13 and 14 are designed so that, due to rodlike elements 5 or 6, pyramidlike bodies 11 or 12 are placed with all their vertices outside the oral cavity in front of the lips, vertices 7 or 7' exhibit a smaller distance from incisors 1 or 2 and vertices 8, 9, and 10 or 8', 9', and 10' each exhibit a larger distance from incisors 1 or 2 and further, in the embodiment shown, the axis of rodlike elements 5 or 6 intersects the triangular surface opposite vertices 7 or 7' and delineated by vertices 8, 9 and 10 or 8', 9' and 10' at an angle of about 90°. Pyramidlike bodies 11 and 12 are furthermore placed so that the triangular surface delineated by vertices 8-10 or 8'-10' each exhibits an upper, essentially horizontal lateral length between vertices 8 and 10 or 8' and 10' with vertex 9 or 9' placed below this lateral length. Pyramidlike bodies 11 and 12 consist of rodlike elements 15 or 16 connected to each other at vertices 7-10 or 7'-10' and each of the same length in the embodiment shown so that even the respective rear vertex 7 or 7' in the viewing direction (arrow A) is completely visible. On rodlike element 16 of reference element 14 connecting vertices 7' and 9' a light source 17 is fastened, which emits a focused light beam 18 vertically upward which, in the measuring arrangement shown, strikes a mirror 19 placed in the plane of vertices 7, 8, and 10 of reference element 13 or fastened to rodlike element 15 there and light beam 18 is reflected forward on this mirror, as indicated by reflected light beam 18'. Since mirror 19 is slanted relative to a horizontal axis in whose direction the axes of rodlike elements 5 and 6 are approximately in the embodiment shown, the reflected light beam shifts upward or downward during a horizontal movement of the lower jaw relative to the upper jaw in this horizontal axial direction (double arrow H), as indicated in FIG. 1 with dotted line 18'', and this shift is a measure of the relative movement of the lower jaw and upper jaw in the direction of double arrow H.

Vertices 7-10 or 7'-10' are, compared with the other parts of reference element 13 or 14, designed to be prominent in contrast or in brightness and/or in coloration and preferably exhibit a coloration which is markedly different from facial color, but also from the color of the lips.

The measuring arrangement furthermore consists of a video camera 20, which is placed at a present distance from the patient sitting on a stool, for example, and is aimed with its lens in viewing direction (arrow A) at the mouth of the patient or at reference elements 13 and 14 fastened on incisors 1 and 2. With the video camera, movement of reference elements 13 and 14 or the displacement of vertices 7-10 and 7'-10' and the change in position of reflected light beam 18' produced during a relative movement between the lower jaw and the upper jaw (chewing, etc.) is recorded. The corresponding video signals are then stored in an image storage device 21, which for example is formed at least partially by a video recorder. With the aid of an electronic switch 22, the frames stored in image storage device 21 can be scanned by line and column and a signal is transmitted to a memory 23 if, during this scanning, one of the prominently designed vertices 7-10 or 7'-10' or reflected light beam 18', especially prominent due to its brightness, is detected. From the respective scanning phases results the position of the vertex or of reflected light beam 18' detected each time so that the electrical signals or data characteristic of this position can be stored in memory 23. The data stored in memory 23 can then be fed to a computer 24 which, from this data, determines the relative movement between the upper jaw and lower jaw according to a suitable program. The data thus obtained can then be channeled to the various further purposes, or for use in the most diverse applications, for example for optical display of the relative movement between lower and upper jaw, for expressing the chronological progress of the various movement components of this relative movement, etc. Furthermore, this data can also be stored and used later for comparison with the relative movement between lower and upper jaw simulated in a dental articulator.

In FIG. 3 a further measuring arrangement is shown, which differs from the measuring arrangement according to FIG. 1 essentially in that in addition to video camera 20 another video camera 25 with associated image storage 26 and associated electronic switch 27 is provided. Image storage device 26 and electronic switch 27 correspond in their function to image storage device 21 and electronic switch 22. Video camera 25 is, in the same way as video camera 20, placed at a preset distance from the patient sitting on a stool, for example, and its lens is aimed in viewing direction (arrow A') at the mouth of the patient or at reference elements 13 and 14 fastened to incisors 1 and 2; however in the embodiment shown in FIG. 3 the optical axes (arrows A and A') of both video cameras 20 and 25 together enclose an angle of 45° which opens toward the side of the measuring arrangement facing video cameras 20 and 25, i.e., opened to the left side in the representation chosen for FIG. 3. The video signals provided by video camera 25 are stored in image storage device 26 which, for example, is in turn at least partially made with a video camera. Of course, another suitable memory can be used for image storage device 26 and image storage device 21. With the aid of electronic switch 27 the frames stored in image storage device 26 can be scanned by line and column and a signal is always transmitted to memory 23 also connected to electronic switch 27 when during this scanning one of the prominently designed vertices 7-10 or 7'-10' which form the reference marks during measurement is detected. From each scanning phase results the position of the vertex determined in turn by video camera 25, so that this position, together with the position of the vertices picked up by video camera 20, can be stored in memory 23. The data stored in memory is then fed to computer 24 which, from this data, in turn determines according to a suitable program the mutual position exhibited by vertices 7-10 or 7'-10' on each reference elements 13 or 14 and the position occupied by individual reference marks 7-10 of reference element 13 relative to reference marks 7'-10' of reference element 14 thus determining the relative movement between the upper jaw and the lower jaw. The embodiment shown in FIG. 3 has the advantage that, for movement in the direction of double arrow H, light source 17 and mirror 19 are not necessary, rather the direction of movement in this horizontal axis can be determined by the optical axes, slanted toward each other, of video cameras 20 and 25.

Of course it is also possible in the embodiment shown in FIG. 3 to connect both video cameras 20 and 25 to a single image storage device exhibiting two channels or memories whose output signal is then evaluated with a single electronic switch in the multiplex process, specifically in an initial period at first the video signal of video camera 20 and in a subsequent period the video signal of video camera 25. Independently of this, in the embodiment according to FIG. 1 and in the embodiment according to FIG. 3, image storage devices 21 or 26 can of course be eliminated and then the signal provided respectively by video camera 20 or 25 is evaluated immediately in a corresponding electronic switch 22 or 27 in the way described above. Independently of this it is further possible to conduct the evaluation of the signals provided by video cameras 20 or 25 or the determination of the position of vertices 7-10 or 7'-10' in such a way that the position of vertices 7-10 or 7'-10' described in the video pictures of video cameras 20 or 25 is compared with a preset optical or electronic grid and, from this comparison, the actual position of the named vertices is determined. This can also occur, for example, in that in electronic switch 22 or 27 an electronic grid is generated such that during the line and column scanning or detection by the corresponding video signal the distance appearing during scanning of the signal corresponding to the one vertex 7-10 or 7'-10' is detected by line and column by a preceding or subsequent grid signal and from this, taking into account this grid signal which defines a certain position, the actual position of the vertex 7-10 or 7'-10' involved is determined. Especially with a correspondingly fine grid division an especially great accuracy in the determination of the actual position of vertices 7-10 or 7'-10' can be achieved in this way.

The measuring arrangement shown in FIG. 3, in which reference elements 13 and 14 are viewed from two viewing directions (A, A') which together enclose an angle, can also be made with a single video camera when the reference marks are viewed with this camera through a mirror device alternating each time from the one viewing direction and next from the other viewing direction, so that in chronological sequence such signals from both viewing directions are fed to the image storage device or to the electronic switch for evaluation of the video signals.

FIG. 4 shows an embodiment in which the determination of the position of vertices 7-10 or 7'-10' occurs not with the aid or one or more video cameras, but with the aid of a laser device 28. This device consists of a laser 29 which emits a point-shaped or highly focused light beam 30 of a preset wavelength, of a deflection or scanning device 31 exhibiting two deflection mirrors for light beam 30, of light detector 32 and of an electronic measuring and evaluation device 33 whose output is in turn connected to memory 23 for computer 24. Laser device 28 is placed at a predetermined distance from the patient sitting on a stool, for example, in such a way that light beam 30' deflected with the deflection device scans by line and column, in two axial directions running mutually perpendicular, for example in the vertical axis and in the transversal axis running perpendicular to the plane of the drawing, the measuring area formed by vertices 7-10 and 7'-10' of reference elements 13 and 14. Light beam 30" thus reflected on light detector 32 is converted in this detector into an electrical signal which is fed to measuring and evaluation device 33, specifically together with a signal derived from deflection device 31 and this signal accounts for the respective spatial angle exhibited by light beam 30', for example, relative to a reference axis. From these signals and optionally from another signal derived from laser 29 or a control device not further shown (based on the respective angular deviation of light beam 30' and on the distance exhibited by reference marks 7-10 or 7'-10' from laser device 28 in horizontal axial direction H) the actual position of these reference marks is determined in the measuring and evaluation device and the corresponding values are transmitted by the measuring and evaluation device to memory 23. The distance measurement necessary for the determination of the position of the reference marks is carried out in the measuring arrangement shown in the same way as is customary with corresponding distance measurement devices which operate with a laser light beam. For this distance measurement the transit time between emitted light beam 30 and the light beam striking detector 32 can, for example, be used in a pulsed laser 29. For the determination of the distance, an angle measurement between vertices 7-10 or 7'-10' each placed on reference elements 13 and 14 at a preset distance to one another can also be used. Furthermore, an interference measurement to determine the distance is also possible.

FIG. 5 shows, in simplified form, a further embodiment of the measuring device which differs from the embodiment according to FIG. 4 in that two laser devices 28 are provided which each synchronously scan the measuring area, i.e., the vertices 7-10 or 7'-10' with a light beam 30', but preferably with various wavelengths. Both laser devices 28 are placed at a spatial distance from each other so that scanning light beams 30' emitted by these laser devices each enclose an angle with each other and thus, from the signals provided by the measuring and evaluation devices 33 of laser devices 28, the respective position of vertices 7-10 or 7'-10' or the change in this position in the horizontal axial direction can be determined without the necessity of the distance measurement by laser device 28 as described above in connection with FIG. 4.

The rotation or movement of scanning light beam 30' can of course in the embodiments according to FIGS. 4 and 5 also be achieved in that laser 29 or a part of the particular laser device 28 exhibiting this laser can be mutually rotated in two spatial axes perpendicular to each other.

Furthermore it is also possible, in principle, in the embodiment shown in FIG. 5 to achieve both scanning light beams 30' in that one light beam emitted from a single laser 29, for example, is divided into both light beams 30' using a semitranparent mirror and in this case both laser devices 28 at least partially form a common device.

FIG. 6 shows a simplified representation of a further embodiment of a measuring device operating with a laser beam. This has a laser 34 which in turn is placed at a distance from the measuring area, i.e., from reference elements 13 and 14 and which emits a focused light beam 35. The method of operation of this measuring arrangement is based essentially on the fact that one of the two bodies whose relative movement is to be measured is stationary and only the other body is moving. Light beam 35 is aimed in this measuring arrangement at a prominent reference mark of the moving body, i.e., for example at vertex 7' of reference element 14 fastened to the lower jaw. The latter occurs either by manual adjustment of laser 34 or by rotating this laser first for achieving a line- and column-scanning movement of light beam 35 and then, when light beam 35' is reflected on light detector 36 by the prominent reference mark, i.e., by vertex 7', the rotation movement of laser 34 is interrupted by a signal generated by this light detector and laser 34 next maintains the most recent position assumed. During movement of vertex 7' laser 34 is carried along or turned so that light beam 35 constantly strikes vertex 7' so that from this turning movement, which laser 34 performs while being carried along, the movement of vertex 7' in the vertical and transversal axial direction, i.e., in the plane perpendicular to the plane of the drawing in FIG. 6, can be very precisely determined. The control criterion for carrying along laser 34 is light beam 35' striking detector 36, i.e., by an automatic electric control driven by detector 36, laser 34 is correspondingly guided so that light beam 35' reflected on detector 36 generates a maximum signal at the output of this detector. To achieve a direction select during the tracking of laser 34, the measuring device exhibits a means which sets the direction of movement of vertex 7' in the respective axial direction. This is, for example, possible by using a photodiode with limiting illuminated field or also by having laser 34 perform, in addition to the tracking movement, an oscillating movement around both axial directions, around which laser 34 is rotated during tracking so that then from the point at which, in this oscillating movement, the maximum of the signal provided by detector 36 strikes, the direction of movement of vertex 7' in both axial directions can be determined.

In connection with a distance measuring device the movement of vertex 7' in the horizontal axial direction can be determined with the measuring device according to FIG. 6. Without this distance measuring device, the measuring arrangement of FIG. 6 is usable when a movement of the reference mark or vertex 7' is to be anticipated in only one plane. The measuring device according to FIG. 6 can, however, also be combined with other previously described measuring devices.

A further embodiment is shown in FIG. 7. In this embodiment, on the upper and lower jaw of head 37 of a patient only the three respective reference marks 8–10 or 8'–10' are provided, which again are spatially staggered and form the vertices of a triangle. Reference marks 8–10 or 8'–10' are formed each on a reference element 38 or 39 and each reference element is provided for fastening on the upper or lower jaw or on the rows of teeth there on a biting fork. To make possible a three-dimensional determination of the relative movement between upper jaw and lower jaw, in this embodiment two optoelectronic devices 40 and 41 are provided, which are placed spatially staggered so that they cover the measuring area formed by reference marks 8–10 and 8'–10' from two different axial directions (viewing axes).

FIG. 8 shows a similar embodiment as in FIG. 7 and in the embodiment according FIG. 8, on the lower jaw there are however two pairs of three reference marks each, formed by reference marks 8'–10' and reference marks 8"–10", and reference marks 8'–10' or 8"–10" of each pair are spatially staggered so that they again form the vertices of a triangle, and both triangles are placed like mirror images at a middle plane M which is vertical and perpendicular to the front side of head 37 and reference marks 10' and 9' or 10" and 9", which form the sides of the triangle adjacent to middle plane M, are each provided in a vertical direction above one another. Reference marks 8'–10' are provided on a reference element 39' and reference marks 8"–10" on a reference element 39". Both reference elements 39' and 39" are fastened separately on the lower jaw, specifically, for example, with the aid of parts 44 and 45 or a two-part biting fork 46, and reference marks 8'–10' are provided on part 44 and reference marks 8"–10" on part 45. This embodiment has the advantage that, with devices 40 and 41, not only is a three-dimensional detection or measurement of the relative movement between the upper jaw and the lower jaw possible, but with these devices, deformations of the lower jaw which occur during movement of the lower jaw or in chewing can be detected. In the embodiment shown in FIGS. 8 and 9 a total of six reference marks 8'–10' and 8"–10" are provided. In principle, a total of five reference marks would be enough. If the deformation of the upper jaw is to be detected, reference marks 8–10 are provided on the lower jaw and reference marks 8'–10' and 8"–10" on the upper jaw.

In the embodiments shown in FIGS. 7 and 8, reference marks 8–10, 8'–10' or 8"–10" are each placed so that the sides of the triangles formed by the reference marks face devices 40 and 41, viewing axes 42 and 43 of these devices placed at a distance from the front side of head 37 form an angle with the side of these triangles.

The invention was explained above based on embodiments. It is understood that changes and modifications are possible without leaving the basic idea of the invention. Thus it is for example also possible that instead of using the reference marks formed by vertices 7–10 or 7'–10' on reference elements 13 and 14, at least on one of the two bodies, for example on the head or skull of the patient, such reference marks can be used which are placed there directly. The light detectors 32 and/or 36 used in the invention are photodiodes or photodiode arrangements or other suitable photoelectric converters which generate an electrical signal when struck by light, as for example phototransistors or photoresistors.

To simplify the localization and/or identification of the reference marks during the determination of the relative movement, these reference marks can also be formed from light-emitting elements (light diodes, for example), which then, for example, emit respectively light of different coloration and/or brightness and/or wavelength and/or modulated light, i.e., intensity-modulated light, and here it can be advantageous for the identification of the individual reference marks that the light emitted from at least a part of the reference marks differs in modulation frequency from the light of the other reference marks.

Of course, prominent points or lines made on reference elements or bodies can also be used as reference marks.

I claim:

1. A process for three-dimensional determination of the relative movement between the jaws, said process comprising steps of
affixing at least one reference element to the teeth of the lower jaw and at least one reference element to the teeth of the upper jaw, with one of said reference elements comprising at least four spatially staggered reference marks arranged in three dimensions and with the other of said reference elements comprising at least three spatially staggered reference marks;
optically detecting the position of each reference mark in relation to each of the other reference marks along at least two viewing axes, and
determining the relative movement of the jaws from the change in the mutual position of the reference marks.

2. A process according to claim 1, wherein the step of determining the relative movement of the jaws is done with the aid of a computer.

3. A process according to claim 1, wherein each of said reference elements comprise at least four spatially staggered reference marks.

4. A process according to claim 1, wherein each of said reference elements is a three-dimensional body and wherein said reference marks are formed by the vertices of said body.

5. A process according to claim 4, wherein the reference elements have the shape of pyramids, and the reference marks are formed by the vertices of said pyramids.

6. A process according to claim 1, wherein the step of optically detecting the relative position of the reference marks includes observing said elements with two video cameras from different viewing angles.

7. A process according to claim 6, comprising a further step of storing images in an image storage device connected to said cameras.

8. A process according to claim 6, wherein images supplied by the video cameras are scanned by line or column to determine the position of the reference marks.

9. An apparatus for determining relative three-dimensional movement between the jaws, said arrangement comprising
at least two reference elements having means for fixedly attaching to the teeth of the lower and upper jaws, respectively,
at least one of these reference elements comprising at least four reference marks, being spatially staggered and being arranged in three dimensions and with another of said reference elements comprising at least three spatially staggered reference marks, whereby the reference marks of the reference elements form a measurement area when the reference elements are attached to said jaws,
an optoelectronic device which is placed at a distance from the measurement area and by which the position of each reference mark in relation to all the other reference marks can be determined.

10. An apparatus according to claim 9, wherein all of said reference elements comprise four spatially staggered reference marks.

11. An apparatus according to claim 9, wherein at least one of said reference elements is a three-dimensional body, said reference marks being formed by vertices thereof.

12. An apparatus according to claim 11, wherein said three-dimensional body is a pyramid, and the reference marks are formed by the vertices of said pyramidical body.

* * * * *